(12) United States Patent
Lee et al.

(10) Patent No.: US 12,198,350 B2
(45) Date of Patent: Jan. 14, 2025

(54) SEGMENTATION SYSTEM AND METHOD OF AN ASCENDING AORTA AND A CORONARY ARTERY FROM CCTA USING A HYBRID APPROACH

(71) Applicant: INDUSTRY-ACADEMIC COOPERATION FOUNDATION, YONSEI UNIVERSITY, Seoul (KR)

(72) Inventors: Joon Sang Lee, Seoul (KR); Jun Hong Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 367 days.

(21) Appl. No.: 17/820,514

(22) Filed: Aug. 17, 2022

(65) Prior Publication Data

US 2023/0281822 A1   Sep. 7, 2023

(30) Foreign Application Priority Data

Mar. 3, 2022 (KR) .......................... 10-2022-0027282

(51) Int. Cl.
G06T 7/11 (2017.01)
A61B 6/00 (2024.01)
(Continued)

(52) U.S. Cl.
CPC ................ *G06T 7/11* (2017.01); *A61B 6/032* (2013.01); *A61B 6/504* (2013.01); *A61B 6/5205* (2013.01);
(Continued)

(58) Field of Classification Search
CPC . G06T 7/11; G06T 7/136; G06T 2207/10081; G06T 2207/20036;
(Continued)

(56) References Cited

U.S. PATENT DOCUMENTS

| 9,311,570 B2 * | 4/2016 | Mohr ........................ G06T 7/11 |
| 9,710,915 B2 * | 7/2017 | Firouzian ............... A61B 6/037 |

(Continued)

FOREIGN PATENT DOCUMENTS

| JP | 2016168126 A | 9/2016 |
| KR | 20170045390 A | 4/2017 |

(Continued)

OTHER PUBLICATIONS

Baumgartner, C. et al., "An Exploration of 2D and 3D Deep Learning Techniques for Cardiac MR Image Segmentation," arXiv Cornell University Website, Available Online at https://arxiv.org/abs/1709.04496, Available as Early as Sep. 13, 2017, 8 pages.

(Continued)

*Primary Examiner* — Michael S Osinski
(74) *Attorney, Agent, or Firm* — McCoy Russell LLP

(57) ABSTRACT

Provided are a segmentation system and method of an ascending aorta and a coronary artery from coronary CT angiography (CCTA) using a hybrid approach, which relates to a technology of extracting only the shape of the coronary artery and ascending aorta from the input coronary CT medical image.

16 Claims, 6 Drawing Sheets

(51) Int. Cl.
  *A61B 6/03* (2006.01)
  *A61B 6/50* (2024.01)
  *G06T 7/136* (2017.01)

(52) U.S. Cl.
  CPC .......... *A61B 6/5217* (2013.01); *A61B 6/5241* (2013.01); *A61B 6/5258* (2013.01); *G06T 7/136* (2017.01); *G06T 2207/10081* (2013.01); *G06T 2207/20036* (2013.01); *G06T 2207/20081* (2013.01); *G06T 2207/20212* (2013.01); *G06T 2207/30101* (2013.01)

(58) Field of Classification Search
  CPC . G06T 2207/20081; G06T 2207/20212; G06T 2207/30101; G06T 7/12; G06T 5/30; G06T 7/13; G06T 7/168; G06T 2207/20061; G06T 2207/20084; G06T 5/00; G06T 7/0012; A61B 6/032; A61B 6/504; A61B 6/5205; A61B 6/5217; A61B 6/5241; A61B 6/5258; A61B 6/481; A61B 6/5211; A61B 6/5229; G06N 3/08; G06N 3/04; G16H 50/20
  See application file for complete search history.

(56) References Cited

U.S. PATENT DOCUMENTS

| | | | | |
|---|---|---|---|---|
| 10,869,644 | B2* | 12/2020 | Zhao | A61B 6/032 |
| 11,151,722 | B2* | 10/2021 | Duchesne | G06T 7/12 |
| 11,744,472 | B2* | 9/2023 | Zhao | G06T 7/11 |
| | | | | 600/481 |
| 11,950,877 | B2* | 4/2024 | Meyer | A61B 5/0263 |
| 2008/0170763 | A1* | 7/2008 | Begelman | A61B 5/02007 |
| | | | | 382/128 |
| 2010/0296709 | A1* | 11/2010 | Ostrovsky-Berman | |
| | | | | G06T 7/162 |
| | | | | 382/128 |
| 2013/0216110 | A1* | 8/2013 | Zheng | G06T 7/0012 |
| | | | | 382/128 |
| 2014/0073977 | A1* | 3/2014 | Grady | A61B 5/14535 |
| | | | | 600/504 |
| 2015/0066818 | A1* | 3/2015 | Choi | A61B 5/7275 |
| | | | | 706/12 |
| 2016/0045180 | A1* | 2/2016 | Kelm | A61B 6/504 |
| | | | | 600/408 |
| 2016/0063175 | A1* | 3/2016 | Choi | A61B 5/02028 |
| | | | | 703/11 |
| 2017/0105694 | A1* | 4/2017 | Grass | A61B 6/06 |
| 2018/0276817 | A1* | 9/2018 | Isgum | G06T 7/10 |
| 2019/0034750 | A1* | 1/2019 | Zhou | G06T 7/155 |
| 2019/0298450 | A1* | 10/2019 | Dasi | G16H 50/50 |
| 2019/0336096 | A1* | 11/2019 | Itu | G16H 50/50 |
| 2020/0060637 | A1* | 2/2020 | Schmitt | G06T 7/0016 |
| 2020/0118306 | A1* | 4/2020 | Ye | G06T 11/003 |
| 2020/0205745 | A1* | 7/2020 | Khosousi | G16H 50/20 |
| 2020/0242758 | A1* | 7/2020 | Zhou | G06T 5/30 |
| 2020/0349712 | A1* | 11/2020 | Siemionow | G06T 7/0012 |
| 2021/0022617 | A1 | 1/2021 | Zhao et al. | |
| 2021/0251490 | A1* | 8/2021 | Abdolmanafi | G06N 20/20 |
| 2021/0334963 | A1* | 10/2021 | Isgum | G16H 50/20 |
| 2022/0284583 | A1* | 9/2022 | Lee | G16H 30/20 |
| 2023/0108647 | A1* | 4/2023 | Tu | A61B 6/507 |
| | | | | 382/130 |
| 2023/0117134 | A1* | 4/2023 | Clifton | G06T 11/003 |
| | | | | 382/131 |
| 2023/0206428 | A1* | 6/2023 | Liu | G06N 3/02 |
| | | | | 382/128 |
| 2024/0130702 | A1* | 4/2024 | Flack | A61B 6/463 |
| 2024/0221156 | A1* | 7/2024 | Wang | A61B 5/02028 |
| 2024/0273723 | A1* | 8/2024 | Tison | A61B 8/0891 |

FOREIGN PATENT DOCUMENTS

| | | |
|---|---|---|
| KR | 101793499 B1 | 11/2017 |
| KR | 20190086282 A | 7/2019 |
| KR | 20190139579 A | 12/2019 |
| KR | 102343889 B1 | 12/2021 |

OTHER PUBLICATIONS

Kim, J. et al., "Combination of hessian matrix-based vessel filter and deep learning approach for the segmentation of ascending aorta and coronary arteries from CCTA," Proceedings of the 2021 Winter Conference Program of the Cardiovascular Engineering, Nov. 17, 2021, Kangwon National University, Chuncheon, 5 pages.

Kim, J. et al., "Anatomic Knowledge-based Hybrid Method for Segmenting Coronary Arteries and Ascending Aorta," Proceedings of the International Conference of Manufacturing Technology Engineers (ICMTE 2022), May 25, 2022, Kintex, Korea, 3 pages.

Cai, W. et al., "Detection of 3D Arterial Centerline Extraction in Spiral CT Coronary Angiography," Journal of Healthcare Engineering, vol. 2021, No. 2670793, Aug. 12, 2021, 16 pages.

* cited by examiner

CIRCLE DETECTED BY APPLYING
HOUGH CIRCLE TRANSFORM

CIRCLE CORRESPONDING TO
ASCENDING AORTA

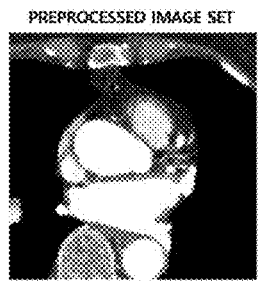
FIG. 8A
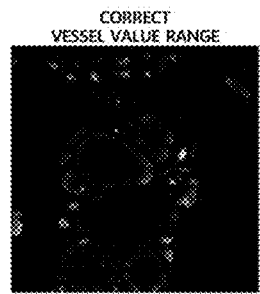
FIG. 8B
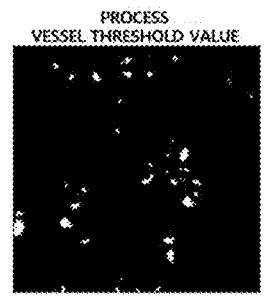
FIG. 8C
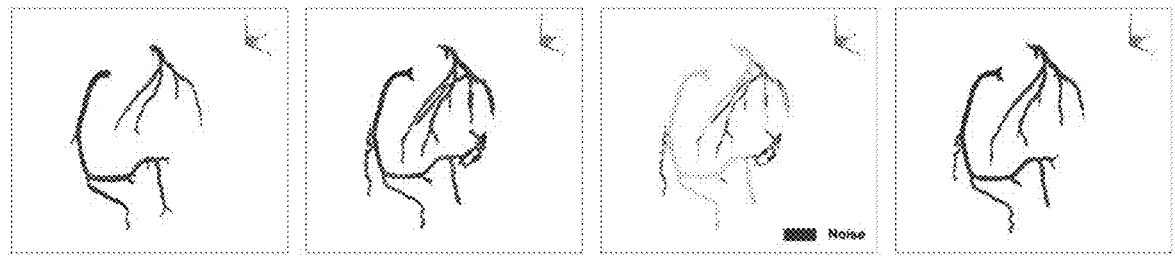
Ground truth
FIG. 9A
$V_\tau(x)$
FIG. 9B
Noise (GT - $V_\tau$)
FIG. 9C
$V_{refined}(x)$
FIG. 9D

SEGMENTATION SYSTEM AND METHOD OF AN ASCENDING AORTA AND A CORONARY ARTERY FROM CCTA USING A HYBRID APPROACH

CROSS-REFERENCE TO RELATED APPLICATION

The present application claims priority to Korean Patent Application No. 10-2022-0027282, filed on Mar. 3, 2022. The entire contents of the above-listed application are hereby incorporated by reference for all purposes.

TECHNICAL FIELD

The following disclosure relates to a segmentation system and method of an ascending aorta and a coronary artery from coronary CT angiography (CCTA) using a hybrid approach, and in particular, to a segmentation system and method of an ascending aorta and a coronary artery from CCTA using a hybrid approach capable of accurately segmenting only the shape of a coronary artery and an ascending aorta for morphological analysis and hemodynamic analysis for coronary artery disease.

BACKGROUND

Statistics Korea reported that heart disease was the second leading cause of death in the cause of death statistics in 2019. In addition, in the global cause of death statistics published by the World Health Organization (WHO) in 2019, heart disease was reported as the highest cause of death. As a result, medical expenses related to heart disease have also gradually increased. According to 'Health Insurance Statistics' published by the Health Insurance Review and Assessment Service, medical expenses due to circulatory system diseases in Korea have increased by an average of 8.4% annually since 2015, reaching about 10 trillion and 500 billion won in 2019.

For this reason, naturally, the need for early diagnosis and accurate diagnosis of heart disease has further emerged.

In clinical practice, medical images such as coronary angiography, coronary CT images, and cardiac MRI have been used for diagnosis, and in particular, a non-invasive, high-resolution, coronary artery CT image that can be scanned at low costs has been most widely used.

For morphological diagnosis of blood vessels, it is necessary to quantitatively analyze the degree of stenosis or the severity of the lesion, and to this end, it is additionally required to accurately extract the lesion from a medical image. Furthermore, by performing hydrodynamic modeling on the extracted blood vessels, it is possible to diagnose in consideration of flow factors.

In particular, fractional flow reserve (FFR), which is widely used in diagnosing coronary artery disease, is a flow factor representing a pressure reduction and may be derived non-invasively by performing predicting through modeling.

In order to perform morphological diagnosis of blood vessels, many studies have been conducted in recognition of the need for segmentation of the ascending aorta and coronary artery in the related art, and a rule-based (RB) method or a deep-learning (DL) method have been utilized.

As the name suggests, the RB method sequentially executes an algorithm according to a pre-established rule, and the DL method derives results through a predictive model learned through artificial intelligence.

However, since each of the RB method and the DL method clearly has advantages and disadvantages, it cannot be determined which method is the better method.

Specifically, since the RB method is not a learning-based method, the RB method does not require a lot of label data, but a processing speed is relatively slow and it is difficult to set a fixed hyper-parameter in an algorithm because there are variations in image quality and shapes of blood vessels depending on the equipment used for image scanning, scan setting conditions, and patients.

Meanwhile, the DL method, which uses a deep learning model, may perform more accurate and faster prediction but requires a large amount of label data to create a learning model. However, in the case of coronary artery CT images, since there is almost no standard label database for, in particular, a coronary artery, it is difficult to obtain a large number of label data, a labeling operation itself takes a lot of time due to a complicated shape of the coronary artery, and related in-depth anatomical knowledge is required as well.

Due to each of these advantages and disadvantages, the RB method is considered to be more suitable for coronary artery segmentation.

Since the ascending aorta has a simpler shape and a larger volume than the coronary artery, labeling is relatively easy and model learning is possible without overfitting. In consideration of this, in the ascending aorta extraction, results may be predicted more quickly and accurately by applying the DL method. However, the related art extracts both the ascending aorta and the coronary artery by selecting either the DL method or the RB method, rather than considering both the DL method and the RB method, so the accuracy is inevitably lowered.

In this regard, Korean Patent No. 10-1793499 ("Aorta extraction method using geometric information of Z-axis image") discloses a technology of effectively extracting a position of the aorta based on geometric information of a Z-axis image obtained from a three-dimensional image of the heart.

RELATED ART DOCUMENT

Patent Document

Korean Patent Registration No. 10-1793499 (Registration date: Oct. 30, 2017)

SUMMARY

An exemplary embodiment of the present disclosure is directed to providing a segmentation system and method of an ascending aorta and a coronary artery from coronary CT angiography (CCTA) using a hybrid approach, capable of segmenting only the shape of the coronary artery and the ascending aorta reasonably, quickly, and accurately from an input coronary CT medical image by collecting only the advantages of a rule-based (RB) method and a deep-learning (DL) method.

In one general aspect, a segmentation system of an ascending aorta and a coronary artery from coronary CT angiography (CCTA) using a hybrid approach includes an image preprocessing unit 100 receiving a 2D coronary artery CT image data set acquired through coronary CT angiography (CCTA) and performing image preprocessing to extract a shape of a coronary artery and ascending aorta, a first processing unit 200 receiving the preprocessed image data set from the image preprocessing unit 100 in a previously stored deep learning model and segmenting an ascending aorta image region, a second processing unit 300 receiving the preprocessed image data set from the image preprocessing unit 100 based on a previously stored rule and segmenting a coronary artery image region using the ascending aorta image region segmented by the first processing unit 200, and a combining unit 400 overlapping the ascending aorta image region and the coronary artery image region to derive a combined structure image.

The image preprocessing unit 100 may include a first brightness adjusting unit 110 adjusting a maximum brightness value and a minimum brightness value based on a preset first brightness value range for each image data, a voxel transforming unit 120 isotropically processing a size of a unit voxel for each image data whose brightness value is adjusted by the first brightness adjusting unit 110 according to a predetermined reference, a noise processing unit 130 removing a noise region for each image data that has been isotropically processed by the voxel transforming unit 120 by applying a morphological closing operator, and a second brightness adjusting unit 140 adjusting a maximum brightness value and a minimum brightness value based on a preset second brightness value range for each image data from which noise has been removed by the noise processing unit 130.

The noise processing unit 130 may include a threshold value processing unit 131 analyzing pixels included in each image data based on a brightness value below a specific threshold value and assigning a predetermined value, an operator applying unit 132 processing each image data by applying a morphological closing operator, a mask generating unit 133 generating a mask by using a predetermined value provided by the threshold value processing unit 131, and a mask processing unit 134 removing a noise region by performing masking on the image data processed by the operator applying unit 132 through a mask by the mask generating unit 133.

The first processing unit 200 may include a deep learning segmenting unit 210 inputting the image data set by the second brightness adjusting unit 140 to the deep learning model trained for ascending aorta segmentation and receiving an image region of ascending aorta, and a segmentation postprocessing unit 220 analyzing an output result from the deep learning segmenting unit 210 and performing noise removal.

The segmentation postprocessing unit 220 may include a filter processing unit 221 applying a preset filter to the output ascending aorta image region to generate an image in which a boundary of an included structure is emphasized, and a transformation processing unit 222 detecting a circular structure included in the image by the filter processing unit 221 by applying a preset transformation technique, wherein the circular structure detected by the transformation processing unit 222 is set as an ascending aorta image region.

The segmentation postprocessing unit 220 may further include a region-of-interest (ROI) processing unit 223 processing the image from the filter processing unit 221 to set an ROI, and an aorta setting unit 224 analyzing the circular structure detected by the transformation processing unit 222 included in the ROI set by the ROI processing unit 223 and setting a final ascending aorta image region in the circular structure detected through a predetermined reference.

The second processing unit 300 may include a vessel calculating unit 310 calculating a vessel value of each pixel constituting each image data preprocessed by the image preprocessing unit 100 by using a hessian-based vessel filter, a vessel correcting unit 320 adjusting a maximum vessel value and a minimum vessel value based on a preset vessel value range using the vessel value from the vessel calculating unit 310 and providing binarized data to each pixel using the adjusted vessel value, a coronary artery extracting unit 330 extracting a structure image region connected to a final ascending aorta image region in the structure image derived through the binarized data given by the vessel correcting unit 320 using the final ascending aorta image region set by the aorta setting unit 224, and a coronary artery setting unit 340 setting as a final coronary artery image region by removing a noise pixel included in the structure image region extracted by the coronary artery extracting unit 330 using the vessel value from the vessel calculating unit 310.

The combining unit 400 may overlap the final ascending aorta image region from the aorta setting unit 224 and the final coronary artery image region from the coronary artery setting unit 340 to derive a structure region combined based on a pixel value at the same position.

In another general aspect, a segmentation method of an ascending aorta and a coronary artery from coronary CT angiography (CCTA) using a hybrid approach using a segmentation system of an ascending aorta and a coronary artery from CCTA using a hybrid approach in which each operation is performed by a calculation processing unit including a computer, includes an image input operation S100 in which an image preprocessing unit receives a 2D CCTA image data set acquired through coronary CT angiography, a preprocessing operation S200 in which the image preprocessing unit performs preprocessing on the image data set based on the image input operation S100, a first processing operation S300 in which a first processing unit segments an ascending aorta image region from the image data set preprocessed by the preprocessing operation S200 using a previously stored deep learning model, a second processing operation S400 in which a second processing unit analyzes the image data set preprocessed in the preprocessing operation S200 and segments a coronary artery image region by using an analysis result and the ascending aorta image region segmented in the first processing operation S300, and a combining operation S500 in which a combining unit overlaps the ascending aorta image region based on the first processing operation S300 and the coronary artery image region based on the second processing operation S400.

The preprocessing operation S200 may include a first brightness adjusting operation S210 of adjusting a maximum brightness value and a minimum brightness value based on a preset first brightness value range for each image data constituting an image data set, a voxel processing operation S220 of isotropically processing a size of a unit voxel for each image data whose brightness value is adjusted in the first brightness adjusting operation S210 according to a predetermined reference, a noise processing operation S230 of removing a noise region for each image data based on the voxel processing operation by applying a morphological closing operator, and a second brightness adjusting operation S240 of adjusting a maximum brightness value and a minimum brightness value based on a preset second brightness value range for each image data from which noise has been removed in the noise processing operation S230.

The noise processing operation S230 may include a threshold value processing operation S231 of analyzing a pixel included in each image data and assigning a predetermined value based on a brightness value below a specific threshold value, an operator applying operation S232 of processing each image data by applying a morphological closing operator, a mask generating operation S233 of generating a mask using a predetermined value given in the threshold value processing operation S231, and a mask processing operation S234 of removing a noise region by performing masking processing on the image data processed in the operator applying operation S232 through the mask in the mask generating operation S233.

The first processing operation S300 may include a deep learning segmenting operation S310 of inputting the image data set based on the second brightness adjusting operation S240 to the deep learning model learning-processed for ascending aorta segmentation and receiving an ascending aorta image region, and a segmentation postprocessing operation S320 of performing noise removal by analyzing an output result based on the deep learning segmenting operation S310.

The segmentation postprocessing operation S320 may include a filter processing operation S321 of generating an image in which a boundary region of the included structure is emphasized by applying a preset filter to the output ascending aorta image region, and a transformation processing operation S322 of detecting the circular structure included in the image based on the filter processing operation S321 by applying a preset transformation technique, wherein the circular structure detected in the transformation processing operation S322 is set as an ascending aorta image region.

The segmentation postprocessing operation S320 may further include a region-of-interest (ROI) processing operation S323 of setting an ROI by processing the image based on the filter processing operation S321, and an aorta setting operation S324 of setting a final ascending aorta image region in the circular structure detected through a predetermined reference by analyzing the circular structure detected by the transformation processing operation S322 included in the ROI set by the ROI processing operation S323.

The second processing operation S400 may include a vessel calculating operation S410 of calculating a vessel value of each pixel constituting each image data preprocessed by the preprocessing operation S200 by using a hessian-based vessel filter, a vessel correcting operation S420 of adjusting a maximum vessel value and a minimum vessel value based on a preset vessel value range using the vessel value based on the vessel calculating operation S410 and providing binarized data to each pixel using the adjusted vessel value, a coronary artery extracting operation S430 of extracting a structure image region connected to a final ascending aorta image region in the structure image derived through the binarized data given by the vessel correcting operation S420 using the final ascending aorta image region set by the aorta setting operation S324, and a coronary artery setting operation S440 of setting as a final coronary artery image region by removing a noise pixel included in the structure image region extracted by the coronary artery extracting operation S430 using the vessel value based on the vessel calculating operation S410.

The combining operation S500 may overlap the final ascending aorta image region based on the aorta setting operation S324 and the final coronary artery image region from the coronary artery setting operation S440 to derive a structure region combined based on a pixel value at the same position.

BRIEF DESCRIPTION OF THE FIGURES

FIGS. 2A to 9D are diagrams illustrating image processing in each configuration by a segmentation system and method of an ascending aorta and a coronary artery from CCTA using a hybrid approach according to an exemplary embodiment of the present disclosure.

DETAILED DESCRIPTION

Figure 1:
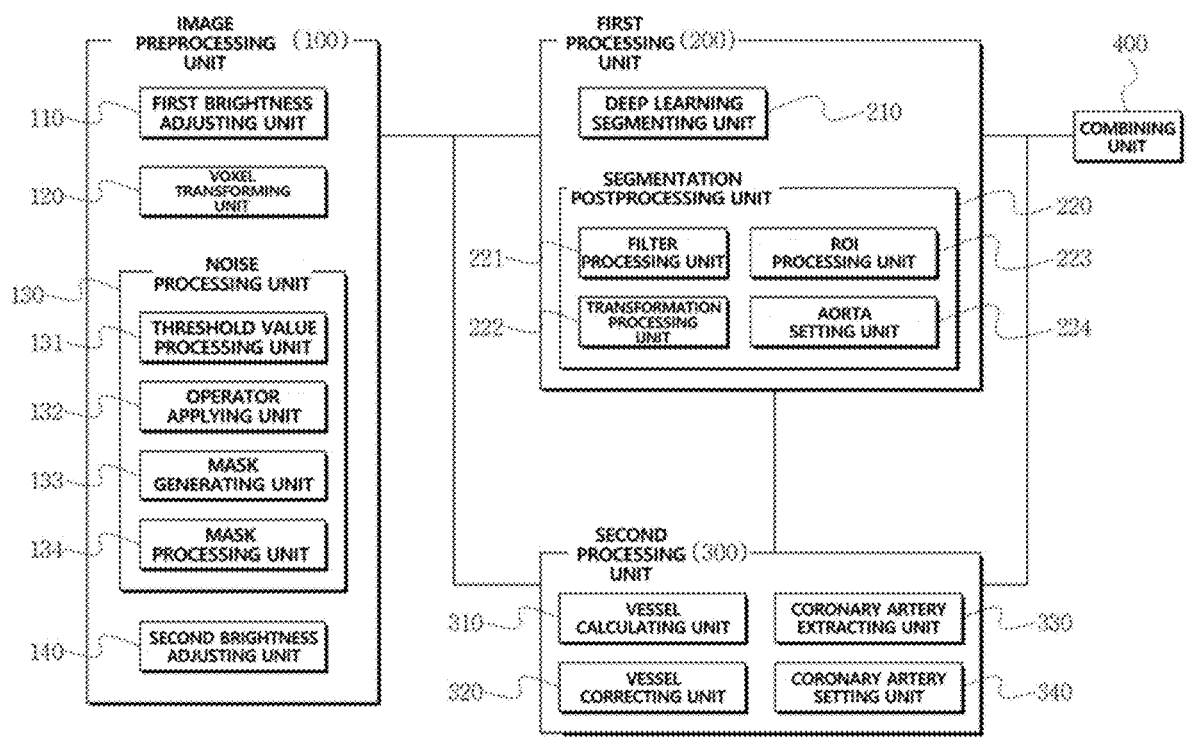
FIG. 1 is an exemplary configuration diagram illustrating a segmentation system of an ascending aorta and a coronary artery from CCTA using a hybrid approach according to an exemplary embodiment of the present disclosure.

Hereinafter, a segmentation system and method of an ascending aorta and a coronary artery from CCTA using a hybrid approach of the present disclosure will be described in detail with reference to the accompanying drawings. The exemplary embodiments of the present disclosure to be introduced below are provided by way of example so that the idea of the present disclosure can be sufficiently transferred to those skilled in the art to which the present disclosure pertains. Accordingly, the scope of the present disclosure is not restricted to the following description and accompanying drawings and may be embodied in another form. In addition, throughout the specification, like reference numerals denote like components.

Here, unless indicated otherwise, the terms used in the specification including technical and scientific terms have the same meaning as those that are usually understood by those who skilled in the art to which the present disclosure pertains, and detailed description of the known functions and constitutions that may obscure the gist of the present disclosure will be omitted.

In addition, the system means a set of components including apparatuses, mechanisms, units, etc. which are organized and regularly interact with each other to perform required functions.

Broadly speaking, a segmentation system and method of an ascending aorta and a coronary artery from CCTA using a hybrid approach according to an exemplary embodiment of the present disclosure are intended to extract only the shape of the coronary artery and ascending aorta from a coronary CT medical image. By using the extracted coronary artery and ascending aorta shape, the degree of stenosis of the cardiovascular vessel may be quantified, and furthermore, the 3D reconstructed blood vessel shape is utilized to diagnose coronary artery disease through hemodynamic modeling. That is, extracting the shape of the coronary artery and ascending aorta is a technology that should precede for morphological and hemodynamic analysis of coronary artery disease.

In the related art, either the RB method or the DL method is selected and used for extraction or an operator has directly performed the process manually, it takes a long time and there is a limitation that the level of anatomical knowledge and subjectivity of the operator may be inevitably reflected.

Accordingly, the segmentation system and method of an ascending aorta and a coronary artery from CCTA using a hybrid approach according to an exemplary embodiment of the present disclosure is a hybrid method that takes only the advantages of the RB method and the DL method, in which, in terms of morphological characteristics, the RB method is applied to the coronary artery extraction and the DL method is applied to the ascending aorta extraction, so that the results (extraction of coronary artery and ascending aorta shape) may be derived rationally, faster, and more accurately.

FIG. 1 is an exemplary configuration diagram showing a segmentation system of an ascending aorta and a coronary artery from CCTA using a hybrid approach according to an exemplary embodiment of the present disclosure. The segmentation system of an ascending aorta and a coronary artery from CCTA using a hybrid approach according to an exemplary embodiment of the present disclosure will be described in detail with reference to FIG. 1.

As shown in FIG. 1, the segmentation system of an ascending aorta and a coronary artery from CCTA using a hybrid approach according to an exemplary embodiment of the present disclosure may include an image preprocessing unit 100, a first processing unit 200, a second processing unit 300, and a combining unit 400, and each component may be included in one arithmetic processing unit or a plurality of arithmetic processing units including a computer.

Each component will be described in detail.

The image preprocessing unit 100 may receive a coronary CT medical image acquired through coronary CT Angiography (CCTA) and performs image preprocessing for extracting a shape of the coronary artery and the ascending aorta.

The coronary CT medical image input from the image preprocessing unit 100 may refer to a two-dimensional (2D) coronary artery CT image data set acquired through the coronary CT angiography, and a three-dimensional (3D) coronary artery CT image may be obtained by stacking the images.

As shown in FIG. 1, the image preprocessing process through the image preprocessing unit 100 is performed by the first brightness adjusting unit 110, the voxel transforming unit 120, the noise processing unit 130, and the second brightness adjusting unit 140.

FIGS. 2A-2E are exemplary diagrams illustrating an image preprocessing process by the image preprocessing unit 100. In detail, FIG. 2A refers to one image data selected from the 2D coronary artery CT image data set input to the image preprocessing unit 100.

Figures 2A, 2B, 2C, 2D, 2E:
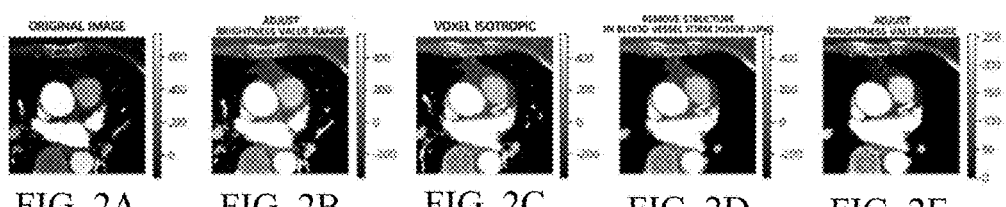

The first brightness adjusting unit 110 performs intensity clipping of image data as shown in FIG. 2B.

In detail, many patients' coronary arteries contain a calcium calcification region, and since the calcium calcification region has a much higher intensity than a vascular region of the coronary artery, extracting the region simply through intensity without considering this may cause a problem that the coronary artery rupture may appear.

In order to prevent this problem in advance, the first brightness adjusting unit 110 performs a process of adjusting the intensity of the calcium calcification region. A maximum brightness value and a minimum brightness value for each pixel constituting each image data constituting the 2D coronary artery CT image data set input to the image preprocessing unit 100 may be adjusted based on a first brightness value range.

The first brightness value range reference set through an experiment can be −350 to 550. Reflecting this, for example, if the brightness value for each pixel is less than −350 HU, the brightness value is adjusted to −350 HU, and if the brightness value is greater than 550 HU, the brightness value is adjusted to 550 HU. Through this, it is desirable to reduce a difference in brightness between the vascular region of the coronary artery and the calcium calcification region by adjusting the brightness values of each pixel constituting each image data to all correspond to −350 to 550 HU. Through this, segmentation accuracy through analysis later may be improved.

In some embodiments, the voxel transforming unit 120 performs voxel isotropy of the image data as shown in FIG. 2C.

In detail, the voxel transforming unit 120 may isotropically process the size of the unit voxel for each image data having a brightness value adjusted by the first brightness adjusting unit 110 according to a predetermined size.

Figure 3:
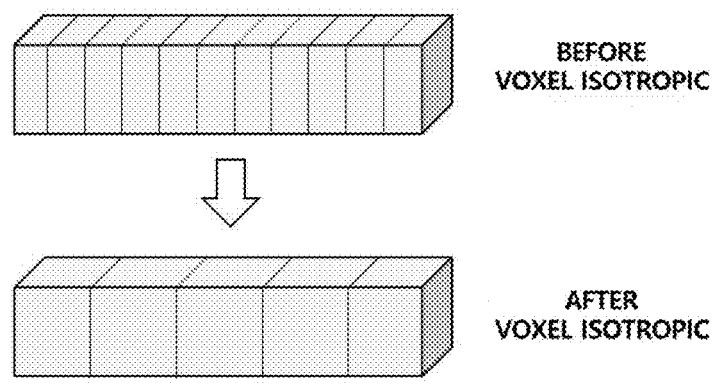

That is, since the width, length, and height of pixels between the respective image data constituting the image data set are different, the size of a unit voxel may be converted to have the same width, length, and height as shown in FIG. 3. This is performed as the voxel is required to be isotropic through preprocessing because the vascular filter to be applied later is basically a 3D-based filter. For example, the size of the unit voxel constituting the image data set is converted into 0.6 mm in width, length, and height.

As shown in FIG. 2D, the noise processing unit 130 may remove a noise region for each image data isotropically processed by the voxel transforming unit 120 by applying a morphological closing operator.

As shown in FIG. 1, the noise processing unit 130 performs an operation through the threshold value processing unit 131, the operator applying unit 132, the mask generating unit 133, and the mask processing unit 134.

In detail, the trachea and bronchi exist inside the lungs and have a shape similar to blood vessels. If these are not removed, there is a high possibility that they are incorrectly detected as a blood vessel region when the blood vessel filter is applied later, and therefore, they are removed in advance through preprocessing to improve segmentation accuracy. It is preferable to use a point that the intensity of the removal objects (trachea, bronchi, etc.) inside the lung is different from that of blood vessels.

Figures 4A, 4B, 4C, 4D, 4E:
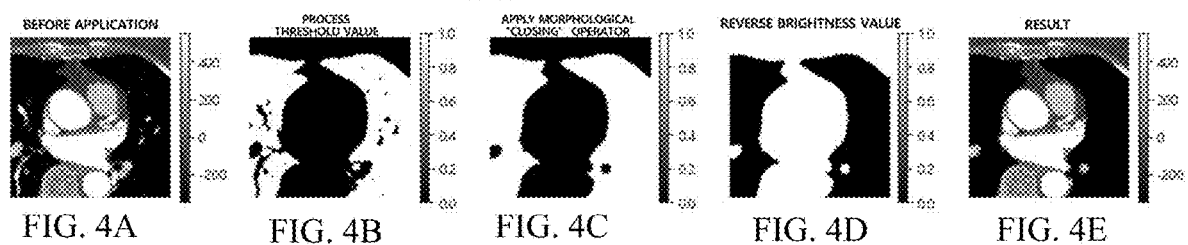

FIG. 4A is an exemplary diagram illustrating each image data isotropically processed by the voxel transforming unit 120. As shown in FIG. 4B, the threshold value processing unit 131 may analyze the pixels included in each image data based on a brightness value below a specific threshold value and assigns a predetermined value to the pixels. That is, a pixel having a brightness value below a specific threshold (which is set to −280 HU through an experiment in the present disclosure) is assigned a value of 1, and a pixel otherwise is assigned a value of 0.

In some embodiments, the operator applying unit 132 processes each image data by applying a morphological closing operator. That is, as shown in FIG. 4C, holes corresponding to the inner region of the lung are filled by applying the morphological closing operator.

In some embodiments, the mask generating unit 133 generates a mask by using a predetermined value assigned by the threshold value processing unit 131. That is, as shown in FIG. 4D, a pixel assigned a value 1 by the threshold value processing unit 131 generates a mask assigned value 0, and a pixel assigned a value 0 generates a mask assigned value 1.

The mask processing unit 134 removes a noise region by performing masking processing on the image data processed by the operator applying unit 132 through a mask generated by the mask generating unit 133. In other words, as shown in FIG. 4E, when the mask generated by the mask generating unit 133 is applied (multiplied) to the image data processed by the operator applying unit 132, a result in which the vascular structure included in the inner region of the lung is removed may be obtained.

Thereafter, the second brightness adjusting unit 140 may adjust a maximum brightness value and a minimum brightness value based on the preset second brightness value range for each image data from which noise is removed by the noise processing unit 130, specifically, by the mask processing unit 134 as shown in FIG. 2E and FIG. 4E.

A reference of the second brightness value range set through an experiment may be 0 to 255. Reflecting this, for example, when the brightness value for each pixel is less than 0 HU, it is adjusted to 0 HU, and when the brightness is greater than 255 HU, it is adjusted to 255 HU. Through this, the brightness values for each pixel constituting each image data are all adjusted to correspond to 0 to 255 HU, thereby improving the segmentation accuracy through analysis later.

In some embodiments, the first processing unit 200 receives the image data set pre-processed by the image preprocessing unit 100 to the deep learning model stored in advance by the DL method, and segments the ascending aorta image region.

As shown in FIG. 1, the first processing unit 200 is configured to include a deep learning segmenting unit 210 and a segmentation postprocessing unit 220.

The deep learning segmenting unit 210 inputs the image data set by the second brightness adjusting unit 140 using the deep learning model trained for ascending aorta segmentation, and outputs the ascending aorta image region.

Since the ascending aorta is a structure having a simple shape and a relatively large volume compared to the coronary artery, results may be quickly derived, while maintaining sufficient segmentation performance through the deep learning model.

Figure 5:
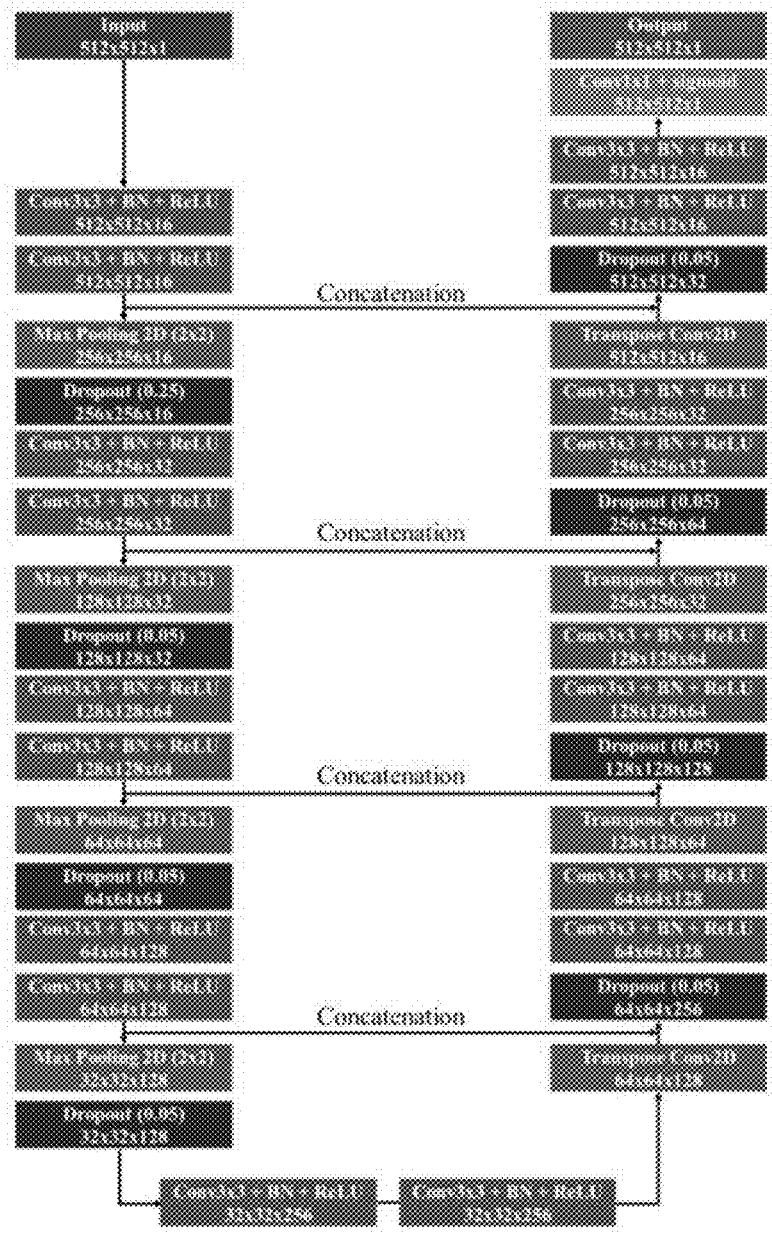

As shown in FIG. 5, the deep learning segmenting unit 210 performs learning processing by adding a dropout layer and a batch normalization layer based on 2D U-Net as a deep learning algorithm as shown in FIG. 5, thereby improving stability and performance of the deep learning model. Of course, the deep learning model may be generated by employing various deep learning algorithms such as undeformed 2D U-Net, 3D U-Net, 2D FCN model, and 3D FCN model, in addition to the deformed 2D U-Net.

The segmentation postprocessing unit 220 may analyze the output result (the ascending aorta segmentation result) by the deep learning segmenting unit 210 and perform noise removal through postprocessing, thereby further improving segmentation accuracy.

In the segmentation postprocessing unit 220, operations are performed in the filter processing unit 221 and the transformation processing unit 222 based on the fact that the ascending aorta basically has a circular cross-section.

Figure 6A:
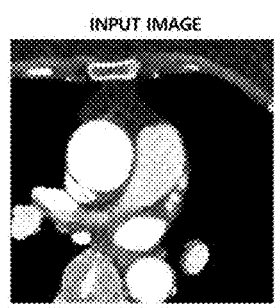

The filter processing unit 221 applies a preset filter to the ascending aorta image region (refer to FIG. 6A) output by the deep learning segmenting unit 210, thereby generating an image in which a boundary of the included structure is emphasized.

Figure 6B:
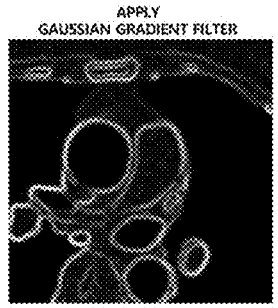

That is, as shown FIG. 6B, the filter processing unit 221 applies a Gaussian gradient filter to the output result (the ascending aorta image region) by the deep learning segmenting unit 210 to obtain an image in which the boundary of the included object (structure) is emphasized.

Figure 6C:
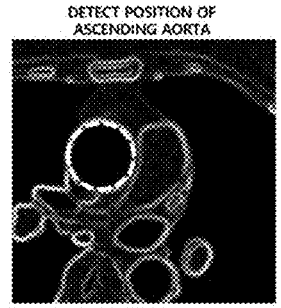

As shown in FIG. 6C, the transformation processing unit 222 applies a Hough circle transform, which is a preset transformation technique, to detect a circular structure for first image data based on the filter processing unit 221. The segmentation postprocessing unit 220 may set the circular structure detected by the transformation processing unit 222 as an ascending aorta image region.

Figure 7A:
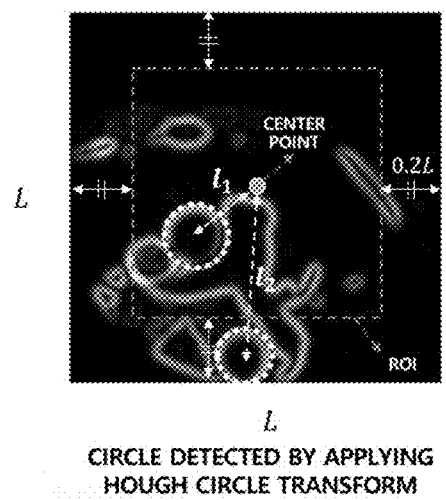

However, as shown in FIG. 7A, in some cases, a plurality of circular structures may be detected on the image data. Among them, it is preferable to perform an additional filtering process to extract only a circular structure corresponding to the ascending aorta.

As shown in FIG. 1, for an additional filtering process, the segmentation postprocessing unit 220 may be configured to further include a region-of-interest (ROI) processing unit 223 and an aorta setting unit 224.

In some embodiments, the ROI processing unit 223 sets an ROI by processing the image based on the filter processing unit 221. As an example, it is preferable to designate the inner region as a ROI by 20% of the horizontal and vertical lengths based on the upper, lower, left, and right corners, and here, the limit of 20% was derived through experiments, but is only an example.

Figure 7B:
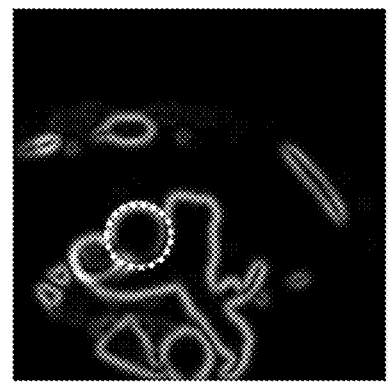

As shown in FIG. 7B, the aorta setting unit 224 may analyze the circular structure detected by the transformation processing unit 222 based on the ROI set by the ROI processing unit 223 to set a final ascending aorta image region in the circular structure detected through a predetermined reference.

In other words, the aorta setting unit 224 analyzes only the circular structure included in the ROI set by the ROI processing unit 223 among the circular structures detected by the transformation processing unit 222, and sets a circle closest based on a center point (center point of ROI) of the image as a final ascending aorta image region, excluding a circular structure in which a radius is 10 mm or less or 20 mm or more.

At this time, except for some circular structures based on the radius, setting the final ascending aorta image region based on the center point is a criterion set in consideration of the position of the ascending aorta through an experiment, but this is also an exemplary embodiment.

The second processing unit 300 may receive the image data set pre-processed by the image preprocessing unit 100 based on a pre-stored rule and segments the coronary artery image region by using the ascending aorta image segmented by the first processing unit 200, as the RB method.

To this end, as shown in FIG. 1, the second processing unit 300 includes a vessel calculating unit 310, a vessel correcting unit 320, a coronary artery extracting unit 330, and a coronary artery setting unit 340.

The vessel calculating unit 310 calculates a vessel value of each pixel constituting each image data preprocessed by the image preprocessing unit 100 by utilizing a hessian-based vessel filter.

In detail, in order to apply a Hessian matrix-based vascular filter, the vessel calculating unit 310 first stacks each image data preprocessed by the image preprocessing unit 100 and applies it as 3D image data, and in this case, a Gaussian smoothing filter is applied so that brightness values between neighboring pixels have a mantissa or distribution.

Thereafter, a Hessian matrix for each pixel and an eigenvalue thereof are calculated. In this case, the Hessian matrix is substituted into Equation 1 below, and the eigenvalue is defined by Equation 2 below.

$$H = \begin{pmatrix} I_{xx} & I_{xy} & I_{xz} \\ I_{yx} & I_{yy} & I_{yz} \\ I_{zx} & I_{zy} & I_{zz} \end{pmatrix} \quad \text{Equation 1}$$

$$0 \approx |\lambda_1| << |\lambda_2| \approx |\lambda_3| \quad \text{Equation 2}$$

Since the Hessian matrix on the 3D image data is calculated, each pixel has 3 eigenvalues. The vessel value of each pixel is calculated by substituting these three eigenvalues to a vessel calculation formula such as Equation 3 proposed by Frangi (Frangi et al, 1998).

$$V(x) = \begin{cases} 0 & \text{if } \lambda_2 > 0 \text{ or } \lambda_3 > 0 \\ \left(1 - \exp\left(-\frac{R_A^2}{2\alpha^2}\right)\right)\exp\left(-\frac{R_B^2}{2\beta^2}\right)\left(1 - \exp\left(-\frac{S^2}{2c^2}\right)\right) & \text{else} \end{cases} \quad \text{Equation 3}$$

(Here, $R_A$ means the sensitivity to a flat plate-shaped structure,
$R_B$ means sensitivity to a speckle-shaped structure, and
S means sensitivity to image contrast.)
$R_A$, $R_B$, and S may be defined by Equation 4 below.

$$R_A = \frac{|\lambda_2|}{|\lambda_3|},$$
$$R_B = \frac{|\lambda_1|}{\sqrt{|\lambda_2 \lambda_3|}},$$
$$S = \sqrt{\sum_{j \leq D} \lambda_j^2}$$

Equation 4

$R_A$, $R_B$, and S are defined by eigenvalues, and it is preferable to perform vascular filter optimization by inputting three hyperparameters (alpha, beta, and gamma) for tuning. Through this, the vessel value has a range of 0 to 1, and as the vessel value is close to 1, it means a pixel close to a center line of the blood vessel.

The vessel correcting unit 320 adjusts the maximum vessel value and the minimum vessel value based on the set vessel value range so that the final ascending aorta region and the coronary artery region set by the aorta setting unit 224 overlap each other by using the vessel value calculated by the vessel calculating unit 310, and assigns binarized data to each pixel using the adjusted vessel value.

In detail, FIG. 8A is each image data preprocessed by the image preprocessing unit 100, and as in FIG. 8B, the range of values after vessel calculation is corrected to 0 to 255, and as shown in FIG. 8C, 1 is assigned to a pixel having a corrected vessel value of 60 or greater and 0 is assigned to the other remaining pixels, thereby obtaining binarized data. Through this, 1 means the blood vessel region and 0 means the remaining region.

The coronary artery extracting unit 330 may extract a structure image region connected to the final ascending aorta image region of the structure image derived through the binarized data assigned by the vessel correcting unit 320 by using the final ascending aorta image region set by the aorta setting unit 224. That is, since the coronary artery is a blood vessel that extends in connection with the ascending aorta, only the structure connected to the final ascending aorta image region set by the aorta setting unit 224, among the blood vessel shape structures segmented through the vessel correcting unit 320, is extracted based thereon. At this time, the extracted structure refers to the coronary artery.

The coronary artery setting unit 340 can set the final coronary artery image region by removing a noise pixel included in the structure image region extracted by the coronary artery extracting unit 330 using the vessel value based on the vessel calculating unit 310.

As shown in FIGS. 9A-9D, the coronary artery setting unit 340 removes noise in the vessel segmentation result by assigning 1 to a pixel recognized as the structure image region by the coronary artery extracting unit 330, while having an intensity of 100 or greater in each pixel constituting each image data preprocessed by the image preprocessing unit 100, and assigning 0 to the remaining pixels.

The combining unit 400 overlaps the ascending aorta image region and the coronary artery image region to derive a combined structure image.

In detail, the combining unit 400 overlaps the final ascending aorta image region set by the aorta setting unit 224 and the final coronary artery image region set by the coronary artery setting unit 340 to derive a coupled structure image.

The final ascending aorta image region set by the aorta setting unit 224 and the final coronary artery image region set by the coronary artery setting unit 340 are in the form of a binarized 2D image data set (1 is a blood vessel, 0 is the rest region). Considering this, if the pixel values at the same position are added after overlapping these two structures, 1 or 2 means a region for the coronary artery or the ascending aorta and 0 corresponds to the rest of the background. Through this, a pixel having a value of 1 or greater is assigned a value of 1, and the remaining pixels are assigned a value of 0, thereby finally deriving a structure in which the ascending aorta and the coronary artery are combined.

Figure 10:
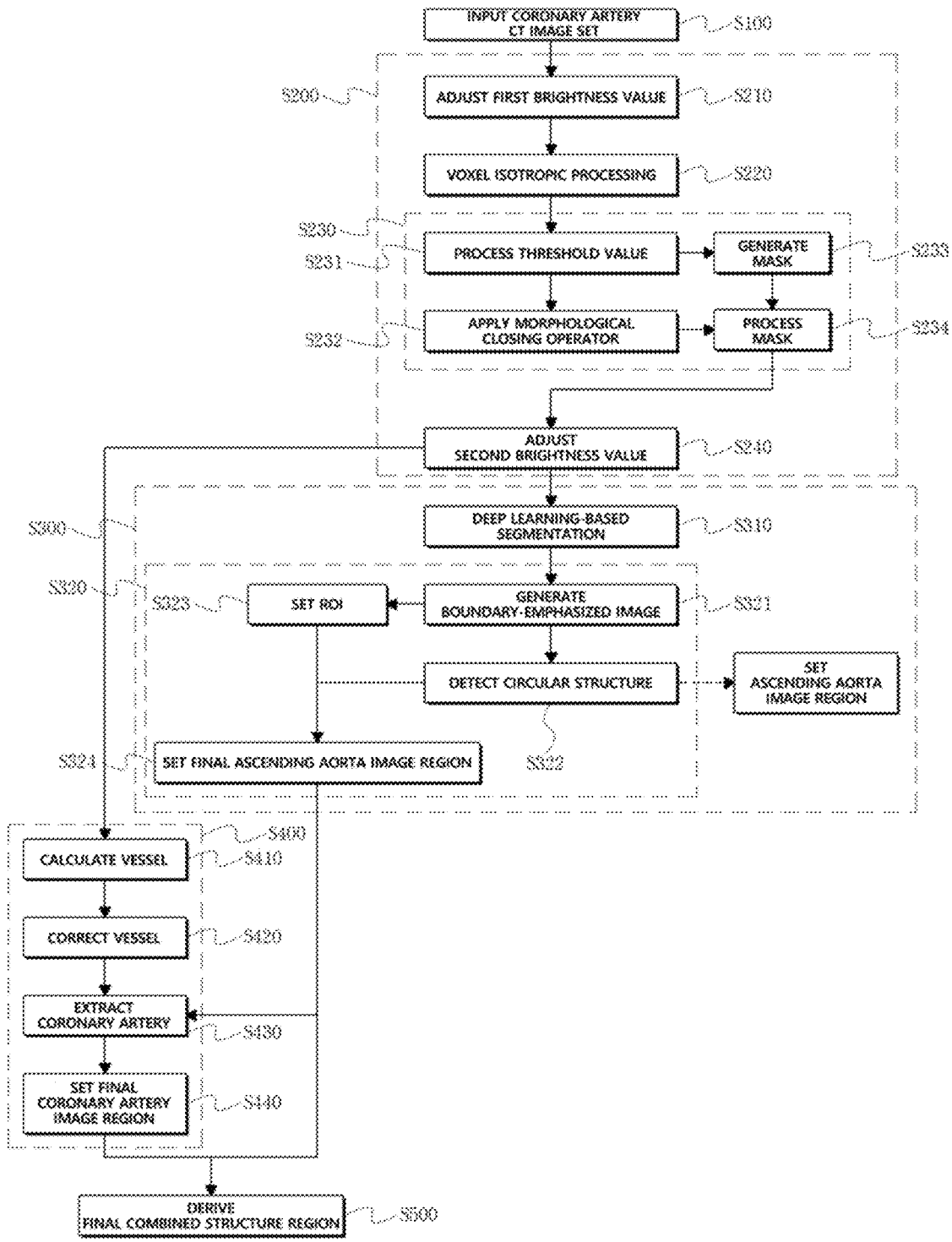
FIG. 10 is a flowchart illustrating a segmentation method of an ascending aorta and a coronary artery from CCTA using a hybrid approach according to an exemplary embodiment of the present disclosure.

FIG. 10 is a flowchart illustrating a segmentation method of an ascending aorta and a coronary artery from CCTA using a hybrid approach according to an exemplary embodiment of the present disclosure. The segmentation method of an ascending aorta and a coronary artery from CCTA using a hybrid approach according to an exemplary embodiment of the present disclosure will be described in detail with reference to FIG. 10.

The segmentation method of an ascending aorta and a coronary artery from CCTA using a hybrid approach according to an exemplary embodiment of the present disclosure is a segmentation method of an ascending aorta and a coronary artery from CCTA using a hybrid approach by using a segmentation system of an ascending aorta and a coronary artery from CCTA using a hybrid approach in which each step is performed by a calculation processing unit including a computer.

As shown in FIG. 10, the segmentation method of an ascending aorta and a coronary artery from CCTA using a hybrid approach according to an exemplary embodiment of the present disclosure includes an image input operation S100, a preprocessing operation S200, a first processing operation S300, a second processing operation S400 and a combining operation S500.

Each operation will be described in detail.

In the image input operation S100, the image preprocessing unit 100 acquires a coronary CT medical image through coronary CT angiography (CCTA).

The coronary artery CT medical image refers to a 2D coronary artery CT image data set acquired through the coronary artery CT angiography, and a 3D coronary artery CT image may be obtained by stacking them.

In the preprocessing operation S200, the image preprocessing unit 100 performs preprocessing on the image data set by the image input operation S100 in order to extract the shape of the coronary artery and the ascending aorta.

In detail, the preprocessing operation S200 includes a first brightness adjusting operation S210, a voxel processing operation S220, a noise processing operation S230, and a second brightness adjusting operation S240, as shown in FIG. 10.

FIG. 2A means one image data selected from the 2D coronary artery CT image data set obtained through the image input operation S100, and in the first brightness adjusting operation S210, intensity clip of image data is performed as shown in FIG. 2B.

In detail, many patients' coronary artery contain a calcium calcification area, and since the calcium calcification area has a much higher intensity than a vascular area of the coronary artery, extracting the area simply through intensity without considering this may cause a problem that the coronary artery rupture may appear.

In order to prevent this problem in advance, a process of adjusting the intensity of the calcium calcification region is performed through the first brightness adjusting operation S210.

In the first brightness adjusting operation S210, a maximum brightness value and a minimum brightness value for each pixel constituting each image data set constituting the 2D coronary artery CT image data set are adjusted based on a preset first brightness value range.

The first brightness value range reference set through an experiment can be −350 to 550. Reflecting this, for example, if the brightness value for each pixel is less than −350 HU, the brightness value is adjusted to −350 HU, and if the brightness value is greater than 550 HU, the brightness value is adjusted to 550 HU. Through this, it is desirable to reduce a difference in brightness between the vascular region of the coronary artery and the calcium calcification area by adjusting the brightness values of each pixel constituting each image data to all correspond to −350 to 550 HU. Through this, segmentation accuracy through analysis later may be improved. In this case, although the reference of the first brightness value range set through an experiment is an optimal range set through an experiment, the present disclosure is not limited thereto.

In the voxel processing operation S220, as shown in FIG. 2C, the size of a unit voxel for each image data having a brightness value adjusted by the first brightness adjusting operation S210 is isotropically processed according to a predetermined size.

That is, since the width, length, and height of pixels between the respective image data constituting the image data set are different, the size of a unit voxel may be converted to have the same width, length, and height as shown in FIG. 3. This is performed as the voxel is required to be isotropic through preprocessing because the vascular filter to be applied later is basically 3D-based filter. For example, the size of the unit voxel constituting the image data set is converted into 0.6 mm in width, length, and height. In this case, the size of the unit voxel is also an optimal size set through an experiment, but is not limited thereto.

In the noise processing operation S230, as shown in FIG. 2D, a noise region for each image data isotropically processed by the voxel transforming unit 120 is removed by applying a morphological closing operator.

As shown in FIG. 10, the noise processing operation S230 includes a threshold value processing operation S231, an operator applying operation S232, a mask generating operation S233, and a mask processing operation S234.

In detail, the trachea and bronchi exist inside the lungs and have a shape similar to blood vessels. If these are not removed, there is a high possibility that they are incorrectly detected as a blood vessel region when the blood vessel filter is applied later, and therefore, they are removed in advance through preprocessing to improve segmentation accuracy. It is preferable to use a point that the intensity of the removal objects (trachea, bronchi, etc.) inside the lung is different from that of blood vessels.

FIG. 4A is an exemplary diagram illustrating each image data isotropically processed by the voxel transforming unit 120. In the threshold value processing operation (S231), as shown in FIG. 4B, the pixels included in each image data may be analyzed based on a brightness value below a specific threshold value and a predetermined value is assigned to the pixels. That is, a pixel having a brightness value below a specific threshold (which is set to −280 HU through an experiment in the present disclosure) is assigned a value of 1, and a pixel otherwise is assigned a value of 0.

In the operator applying operation S232, each image data is processed by applying a morphological closing operator. That is, as shown in FIG. 4C, holes corresponding to the inner region of the lung are filled by applying the morphological closing operator.

In the mask generating operation S233, a mask is generated using the predetermined value assigned by the threshold value processing operation S231. That is, as shown in FIG. 4D, a pixel assigned a value 1 by the threshold value processing unit 131 generates a mask assigned value 0, and a pixel assigned a value 0 generates a mask assigned value 1.

In the mask processing operation S234, a noise region is removed by performing masking processing through the mask generated by the mask generating operation S233 on the image data processed in the operator applying operation S232. In other words, as shown in FIG. 4E, when the mask generated in the mask generating operation S233 is applied (multiplied) to the image data processed in the operator applying operation S232, a result in which the vascular structure included in the inner region of the lung is removed may be obtained.

In the second brightness adjusting operation S240, a maximum brightness value and a minimum brightness value may be adjusted based on the preset second brightness value range for each image data from which noise is removed in the noise processing operation S230 as shown in FIG. 2E and FIG. 4E.

A reference of the second brightness value range set through an experiment may be 0 to 255. Reflecting this, for example, when the brightness value for each pixel is less than 0 HU, it is adjusted to 0 HU, and when the brightness is greater than 255 HU, it is adjusted to 255 HU. Through this, the brightness values for each pixel constituting each image data are all adjusted to correspond to 0 to 255 HU, thereby improving the segmentation accuracy through analysis later. In this case, although the reference of the second brightness value range set through an experiment is an optimal range set through an experiment, the present disclosure is not limited thereto.

In the first processing operation S300, the first processing unit 200 receives the image data set preprocessed in the preprocessing operation S200 by using a pre-stored deep learning model in the DL method, and segments an ascending aorta image region.

In the first processing operation S300, as shown in FIG. 10, a deep learning segmenting operation S310 and a segmentation postprocessing operation S320 are performed.

In the deep learning segmenting operation S310, the image data set by the second brightness adjusting operation S240 is input using the deep learning model trained for ascending aorta segmentation, and the ascending aorta image region is output.

Since the ascending aorta is a structure having a simple shape and a relatively large volume compared to the coronary artery, results may be quickly derived, while maintaining sufficient segmentation performance through the deep learning model.

As shown in FIG. 5, learning processing is performed by adding a dropout layer and a batch normalization layer based on 2D U-Net as a deep learning algorithm by a deep learning algorithm for generating a deep learning model, thereby improving stability and performance of the deep learning model. Of course, the deep learning model may be generated by employing various deep learning algorithms such as an undeformed 2D U-Net, 3D U-Net, 2D FCN model, and 3D FCN model, in addition to the deformed 2D U-Net.

In the segmentation postprocessing operation S320, the output result (the ascending aorta segmentation result) by the deep learning segmenting operation S310 may be analyzed and noise removal is performed through postprocessing, thereby further improving segmentation accuracy.

In the segmentation postprocessing operation S320, the filter processing operation S321 and the transformation processing operation S322 are performed on the basis that the ascending aorta has a circular cross-section.

In the filter processing operation S321, an image in which a boundary of the included structure is emphasized is generated by applying a preset filter to the output result (ascending aorta segmentation result) based on the deep learning segmenting operation S310.

That is, as shown in FIG. 6B, an image in which the boundary of the included object (structure) is emphasized is obtained by applying a Gaussian gradient filter to the output result (the ascending aorta image region) in the deep learning segmenting operation S310.

In the transformation processing operation S322, as shown in FIG. 6C, a circular structure for first image data based on the filter processing operation S321 is detected by applying a Hough circle transform, which is a preset transformation technique. In this case, the detected circular structure may be set as the ascending aorta image region.

However, as shown in FIG. 7A, in some cases, a plurality of circular structures may be detected on the image data. Among them, it is preferable to perform an additional filtering process to extract only a circular structure corresponding to the ascending aorta.

For the additional filtering process, as shown in FIG. 10, the ROI processing operation S323 and the aorta setting operation S324 are performed.

In the ROI processing operation S323, an ROI is set by processing the image based on the filter processing operation S321. As an example, the inner region by 20% of the horizontal and vertical lengths based on the upper, lower, left, and right corners is set as an ROI, and here, the limit of 20% was derived through experiments, but is only an example.

In the aorta setting operation S324, as shown in FIG. 7B, the circular structure detected in the transformation processing operation S322 is analyzed based on the ROI set in the ROI processing operation S323 to set a final ascending aorta image region in the circular structure detected through a predetermined reference.

In other words, in the aorta setting operation S324, only the circular structure included in the ROI set in the ROI processing operation S323 among the circular structures detected in the transformation processing operation S322 is analyzed, and a circle closest based on a center point (center point of ROI) of the image, excluding a circular structure in which a radius is 10 mm or less or 20 mm or more, is set as a final ascending aorta image region.

At this time, except for some circular structures based on the radius, setting the final ascending aorta image region based on the center point is a criterion set in consideration of the position of the ascending aorta through an experiment, but this is also an exemplary embodiment.

In the second processing operation S400, the second processing unit 300 analyzes the image data set preprocessed in the preprocessing operation S200 based on a pre-stored rule in the RB method, and the coronary artery image region is segmented by using an analysis result and the ascending aorta image region segmented in the first processing operation S300.

In the second processing operation S400, as shown in FIG. 10, a vessel calculating operation S410, a vessel correcting operation S420, the coronary artery extracting operation S430, and a coronary artery setting operation S440 are performed.

In the vessel calculating operation S410, a vessel value of each pixel constituting each image data of an image data set preprocessed in the image preprocessing operation S200 is calculated by utilizing a hessian-based vessel filter.

In detail, first, in order to apply a Hessian matrix-based vascular filter, each preprocessed image data is stacked and applied as 3D image data, and in this case, a Gaussian smoothing filter is applied so that brightness values between neighboring pixels have a mantissa or distribution.

Thereafter, a Hessian matrix for each pixel and an eigenvalue thereof are calculated. In this case, the Hessian matrix is substituted into Equation 1 below, and the eigenvalue is defined by Equation 2 above.

Since the Hessian matrix on the 3D image data is calculated, each pixel has 3 eigenvalues. The vessel value of each pixel is calculated by substituting these three eigenvalues to a vessel calculation formula such as Equation 3 proposed by Frangi (Frangi et al, 1998).

$R_A$, $R_B$, and S are defined by eigenvalues, and it is preferable to perform vascular filter optimization by inputting three hyperparameters (alpha, beta, and gamma) for tuning. Through this, the vessel value has a range of 0 to 1, and as the vessel value is close to 1, it means a pixel close to a center line of the blood vessel.

In the vessel correcting operation S420, a maximum vessel value and a minimum vessel value are adjusted based on a preset vessel value range using the vessel value obtained in the vessel calculating operation S410, and binarized data is assigned to each pixel using the adjusted vessel value.

In detail, FIG. 8A is each image data that has been pre-processed, and as in FIG. 8B, the range of values after vessel calculation is corrected to 0 to 255, and as shown in FIG. 8C, 1 is assigned to a pixel having a corrected vessel value of 60 or greater and 0 is assigned to the other remaining pixels, thereby obtaining binarized data. Through this, 1 means the blood vessel region and 0 means the remaining region.

In the coronary artery extracting operation S430, a structure image region connected to the final ascending aorta image region of the structure image derived through the binarized data assigned in the vessel correcting operation S420 is extracted by using the final ascending aorta image region set in the aorta setting operation S324.

That is, since the coronary artery is a blood vessel that extends in connection with the ascending aorta, only the structure connected to the final ascending aorta image region set in the aorta setting operation S324 among the blood vessel shape structures segmented through the vessel correcting operation S420 based thereon. At this time, the extracted structure refers to the coronary artery.

In the coronary artery setting operation S440, the final coronary artery image region is set by removing a noise pixel included in the structure image region extracted in the coronary artery extracting operation S430 by using the vessel value obtained in the vessel calculating operation S410.

That is, as shown in FIG. 10, 1 is assigned to the pixel recognized as the structure image region in the coronary artery extracting operation S430, while having an intensity of 100 or greater in each pixel constituting each image data which has been preprocessed, and 0 is assigned to the remaining pixels, thereby removing noise from the blood vessel segmentation result.

In the combining operation S500, a combined structure image is derived by overlapping the ascending aorta image region and the coronary artery image region.

In detail, in the combining operation S500, the final ascending aorta image region set in the aorta setting operation S324 and the final coronary artery image region set in the coronary artery setting operation S440 overlap to derive a coupled structure image.

The final ascending aorta image region and the final coronary artery image region are in the form of a binarized 2D image data set (1 is a blood vessel, 0 is the remaining region). Considering this, if the pixel values at the same position are added after overlapping these two structures, 1 or 2 means a region for the coronary artery or the ascending aorta and 0 corresponds to the rest of the background. Through this, a pixel having a value of 1 or greater is assigned a value of 1, and the remaining pixels are assigned a value of 0, thereby finally deriving a structure in which the ascending aorta and the coronary artery are combined.

In the segmentation system and method of an ascending aorta and a coronary artery from CCTA using a hybrid approach of the present disclosure based on the configuration described above, the hybrid approach in which the RB method and the DL method are mixed is used according to the characteristics of the coronary artery and the ascending aorta, thereby extracting a result reasonably, quickly, and accurately (extracting the coronary and ascending aorta regions).

Hereinabove, although the present disclosure has been described by specific matters such as detailed components, exemplary embodiments, and the accompanying drawings, they have been provided only for assisting in the entire understanding of the present disclosure. Therefore, the present disclosure is not limited to the exemplary embodiments. Various modifications and changes may be made by those skilled in the art to which the present disclosure pertains from this description.

DETAILED DESCRIPTION OF MAIN ELEMENTS

100: image preprocessing unit
110: first brightness adjusting unit
120: voxel transforming unit
130: noise processing unit
140: second brightness adjusting unit
131: threshold value processing unit
132: operator applying unit
133: mask generating unit
134: mask processing unit
200: first processing unit
210: deep learning segmenting unit
220: segmentation postprocessing unit
221: filter processing unit
222: transformation processing unit
223: ROI processing unit
224: aorta setting unit
300: second processing unit
310: vessel calculating unit
320: vessel correcting unit
330: coronary artery extracting unit
340: coronary artery setting unit
400: combining unit

The invention claimed is:

1. A segmentation system of an ascending aorta and a coronary artery from coronary CT angiography (CCTA) using a hybrid approach, the segmentation system comprising:
an image preprocessing unit receiving a 2D coronary artery CT image data set acquired through a coronary CT angiography (CCTA) and performing image preprocessing to extract a shape of a coronary artery and ascending aorta;
a first processing unit receiving the preprocessed image data set from the image preprocessing unit in a previously stored deep learning model and segmenting an ascending aorta image region;
a second processing unit receiving the preprocessed image data set from the image preprocessing unit based on a previously stored rule and segmenting a coronary artery image region using the ascending aorta image region segmented by the first processing unit; and
a combining unit overlapping the ascending aorta image region and the coronary artery image region to derive a combined structure image.

2. The segmentation system of claim 1, wherein the image preprocessing unit includes:
a first brightness adjusting unit adjusting a maximum brightness value and a minimum brightness value based on a preset first brightness value range for each image data;
a voxel transforming unit isotropically processing a size of a unit voxel for each image data whose brightness value is adjusted by the first brightness adjusting unit according to a predetermined reference;
a noise processing unit removing a noise region for each image data that has been isotropically processed by the voxel transforming unit by applying a morphological closing operator; and
a second brightness adjusting unit adjusting a maximum brightness value and a minimum brightness value based on a preset second brightness value range for each image data from which noise has been removed by the noise processing unit.

3. The segmentation system of claim 2, wherein the noise processing unit includes:
a threshold value processing unit analyzing pixels included in each image data based on a brightness value below a specific threshold value and assigning a predetermined value;
an operator applying unit processing each image data by applying a morphological closing operator;
a mask generating unit generating a mask by using a predetermined value provided by the threshold value processing unit; and a mask processing unit removing a noise region by performing masking on the image data processed by the operator applying unit through a mask by the mask generating unit.

4. The segmentation system of claim 2, wherein the first processing unit includes:
a deep learning segmenting unit inputting the image data set by the second brightness adjusting unit to the deep learning model trained for ascending aorta segmentation and receiving an image region of ascending aorta; and
a segmentation postprocessing unit analyzing an output result from the deep learning segmenting unit and performing noise removal.

5. The segmentation system of claim 4, wherein the segmentation postprocessing unit includes:
a filter processing unit applying a preset filter to the output ascending aorta image region to generate an image in which a boundary of an included structure is emphasized; and
a transformation processing unit detecting a circular structure included in the image by the filter processing unit by applying a preset transformation technique,
wherein the circular structure detected by the transformation processing unit is set as an ascending aorta image region.

6. The segmentation system of claim 5, wherein the segmentation postprocessing unit further includes:
a region-of-interest (ROI) processing unit processing the image from the filter processing unit to set an ROI; and
an aorta setting unit analyzing the circular structure detected by the transformation processing unit included in the ROI set by the ROI processing unit and setting a final ascending aorta image region in the circular structure detected through a predetermined reference.

7. The segmentation system of claim 6, wherein the second processing unit includes:
a vessel calculating unit calculating a vessel value of each pixel constituting each image data preprocessed by the image preprocessing unit by using a hessian-based vessel filter;
a vessel correcting unit adjusting a maximum vessel value and a minimum vessel value based on a preset vessel value range using the vessel value from the vessel calculating unit and providing binarized data to each pixel using the adjusted vessel value;
a coronary artery extracting unit extracting a structure image region connected to a final ascending aorta image region in the structure image derived through the binarized data given by the vessel correcting unit using the final ascending aorta image region set by the aorta setting unit; and
a coronary artery setting unit setting as a final coronary artery image region by removing a noise pixel included in the structure image region extracted by the coronary artery extracting unit using the vessel value from the vessel calculating unit.

8. The segmentation system of claim 7, wherein the combining unit overlaps the final ascending aorta image region from the aorta setting unit and the final coronary artery image region from the coronary artery setting unit to derive a structure region combined based on a pixel value at the same position.

9. A segmentation method of an ascending aorta and a coronary artery from coronary CT angiography (CCTA) using a hybrid approach using a segmentation system of an ascending aorta and a coronary artery from CCTA using a hybrid approach in which each operation is performed by a calculation processing unit including a computer, the segmentation method comprising:
an image input operation in which an image preprocessing unit receives a 2D CCTA image data set acquired through a coronary CT angiography;
a preprocessing operation in which the image preprocessing unit performs preprocessing on the image data set based on the image input operation;
a first processing operation in which a first processing unit segments an ascending aorta image region from the image data set preprocessed by the preprocessing operation using a previously stored deep learning model;
a second processing operation in which a second processing unit analyzes the image data set preprocessed in the preprocessing operation and segments a coronary artery image region by using an analysis result and the ascending aorta image region segmented in the first processing operation; and
a combining operation in which a combining unit overlaps the ascending aorta image region based on the first processing operation and the coronary artery image region based on the second processing operation.

10. The segmentation method of claim 9, wherein the preprocessing operation includes:
a first brightness adjusting operation of adjusting a maximum brightness value and a minimum brightness value based on a preset first brightness value range for each image data constituting an image data set;
a voxel processing operation of isotropically processing a size of a unit voxel for each image data whose brightness value is adjusted in the first brightness adjusting operation according to a predetermined reference;
a noise processing operation of removing a noise region for each image data based on the voxel processing operation by applying a morphological closing operator; and
a second brightness adjusting operation of adjusting a maximum brightness value and a minimum brightness value based on a preset second brightness value range for each image data from which noise has been removed in the noise processing operation.

11. The segmentation method of claim 10, wherein the noise processing operation includes:
a threshold value processing operation of analyzing a pixel included in each image data and assigning a predetermined value based on a brightness value below a specific threshold value;
an operator applying operation of processing each image data by applying a morphological closing operator;
a mask generating operation of generating a mask using a predetermined value given in the threshold value processing operation; and
a mask processing operation of removing a noise region by performing masking processing on the image data processed in the operator applying operation through the mask in the mask generating operation.

12. The segmentation method of claim 10, wherein the first processing operation includes:
a deep learning segmenting operation of inputting the image data set based on the second brightness adjusting operation to the deep learning model learning-processed for ascending aorta segmentation and receiving an ascending aorta image region; and a segmentation postprocessing operation of performing noise removal by analyzing an output result based on the deep learning segmenting operation.

13. The segmentation method of claim 12, wherein the segmentation postprocessing operation includes:

a filter processing operation of generating an image in which a boundary region of the included structure is emphasized by applying a preset filter to the output ascending aorta image region; and a transformation processing operation of detecting the circular structure included in the image based on the filter processing operation by applying a preset transformation technique, wherein the circular structure detected in the transformation processing operation is set as an ascending aorta image region.

14. The segmentation method of claim 13, wherein the segmentation postprocessing operation further includes:

a region-of-interest (ROI) processing operation of setting an ROI by processing the image based on the filter processing operation; and an aorta setting operation of setting a final ascending aorta image region in the circular structure detected through a predetermined reference by analyzing the circular structure detected by the transformation processing operation included in the ROI set by the ROI processing operation.

15. The segmentation method of claim 14, wherein the second processing operation includes:

a vessel calculating operation of calculating a vessel value of each pixel constituting each image data preprocessed by the preprocessing operation by using a hessian-based vessel filter;

a vessel correcting operation of adjusting a maximum vessel value and a minimum vessel value based on a preset vessel value range using the vessel value based on the vessel calculating operation and providing binarized data to each pixel using the adjusted vessel value;

a coronary artery extracting operation of extracting a structure image region connected to a final ascending aorta image region in the structure image derived through the binarized data given by the vessel correcting operation using the final ascending aorta image region set by the aorta setting operation; and a coronary artery setting operation of setting as a final coronary artery image region by removing a noise pixel included in the structure image region extracted by the coronary artery extracting operation using the vessel value based on the vessel calculating operation.

16. The segmentation method of claim 15, wherein the combining operation overlaps the final ascending aorta image region based on the aorta setting operation and the final coronary artery image region from the coronary artery setting operation to derive a structure region combined based on a pixel value at the same position.

* * * * *